US009328370B2

(12) United States Patent
Chang et al.

(10) Patent No.: US 9,328,370 B2
(45) **Date of Patent: *May 3, 2016**

(54) RECOMBINANT BACTERIA RECOGNIZING PROTEIN AND USES THEREOF

(71) Applicant: SIMPSON BIOTECH CO., LTD., Taoyuan County (TW)

(72) Inventors: Margaret Dah-Tsyr Chang, Taipei (TW); Chia-Chin Sheu, Taoyuan County (TW)

(73) Assignee: SIMPSON BIOTECH CO., LTD., Taoyuan County (TW)

( * ) Notice: Subject to any disclaimer, the term of this patent is extended or adjusted under 35 U.S.C. 154(b) by 1 day.

This patent is subject to a terminal disclaimer.

(21) Appl. No.: 14/275,908

(22) Filed: May 13, 2014

(65) Prior Publication Data

US 2014/0343250 A1 Nov. 20, 2014

Related U.S. Application Data

(60) Provisional application No. 61/823,531, filed on May 15, 2013.

(51) Int. Cl.

| | |
|---|---|
| ***C12P 21/02*** | (2006.01) |
| ***C07K 14/00*** | (2006.01) |
| ***C07K 14/435*** | (2006.01) |
| ***C12N 15/62*** | (2006.01) |

(52) U.S. Cl.
CPC ................ *C12P 21/02* (2013.01); *C07K 14/00* (2013.01); *C07K 14/001* (2013.01); *C07K 14/43509* (2013.01); *C12N 15/62* (2013.01); *C07K 2319/33* (2013.01); *C07K 2319/35* (2013.01)

(58) Field of Classification Search
None
See application file for complete search history.

*Primary Examiner* — Ja'Na Hines
*Assistant Examiner* — Khatol Shahnan Shah
(74) *Attorney, Agent, or Firm* — Hannah M. Tien

(57) ABSTRACT

The present invention relates to a recombinant protein comprising SEQ ID NO: 1 and a bacteria recognizing lectin. The present invention also relates to uses of the recombinant protein comprising detecting pathogens, removing endotoxins, determining the presence of an endotoxin or endotoxin-like material, and determining the presence of pathogen-associated molecular pattern (PAMP) comprising rhamnose-rhamnose (Rha-Rha), rhamnose-N-acetyl-mannosamine (Rha-ManNAc), N-acetyl-mannosamine-rhamnose (ManNAc-Rha), rhamnose-galatose (Rha-Gal), or galatose-rhamnose (Gal-Rha) in a sample, and use as a medicament, a disinfectant, a decontaminant, a surfactant or a diagnostic means. The present invention further relates to a method for prevention and/or treatment of conditions related to pathogen related infections in a patient in need thereof comprising: administering to said patient a pharmaceutically effective amount of composition comprising the recombinant protein, wherein the recombinant protein functions as an antagonist of PAMP comprising Rha-Rha, Rha-ManNAc, ManNAc-Rha, Rha-Gal, or Gal-Rha.

23 Claims, 5 Drawing Sheets

A

B

A

B

RECOMBINANT BACTERIA RECOGNIZING PROTEIN AND USES THEREOF

CROSS-REFERENCES TO RELATED APPLICATIONS

The present application is a regular application which claims priority to U.S. Provisional Application No. 61/823,531, filed on May 15, 2013, incorporated herein by reference in its entirety.

FIELD OF THE INVENTION

The present invention relates to a novel recombinant protein comprising an artificial peptide and a bacteria recognizing lectin (BRL), and uses thereof.

The sequence listing text file, file name 2306_SQ_SEQlist_ST25, created May 9, 2014, file size 6,285 bytes, is incorporated herein by reference in its entirety.

BACKGROUND OF THE INVENTION

Lectins are a group of carbohydrate-binding proteins capable of recognizing specific carbohydrate structures and widely distributed in living organisms. Animal lectins are classified into various families according to their sequence similarities in carbohydrate-recognition domains (CRDs) and sugar-binding specificities. They play roles in a variety of physiological processes, functioning as cell surface receptors, involving in interactions between cells during development and differentiation or taking part in recognition of foreign molecules during immune responses. In recent years, biochemical and physiological properties of humoral lectins from marine resources have been thoroughly investigated. Lectins from marine organism such as plasma lectins from Horseshoe crab can recognize lipopolysaccharide (LPS). LPS typically consists of a hydrophobic domain known as lipid A (or endotoxin), a nonrepeating "core" oligosaccharide, and a distal polysaccharide (or O-antigen). BRL, a bacteria-recognizing and LPS-binding protein, is a hemolymph protein isolated from *Tachypleus tridentatus* in Taiwan. BRL shows a 68% sequence identity with tachylectin-3, a lectin isolated from the amebocytes of Japanese *T. tridentatus*. Native BRL isolated from hemolymph is capable of binding to three species of bacteria, *Streptococcus pneumoniae* R36A (Gram-positive), *Vibrio parahaemolyticus* (Gram-negative), and *Escherichia coli* Bos-12 (Gram-negative) in a dose-dependent and saturable manner. Native BRL purified from the plasma of Taiwanese *T. tridentatus* was consisted of different glycosylated and partially-protease-cleaved forms which caused difficulties in determining the exact moiety possessing bacterial binding activity. Since horseshoe crab is an ancient marine arthropod and isolation of native BRL directly from hemolymph does not conform to humanism, recombinant BRL (rBRL) has been engineered and expressed by a yeast strain *P. pastoris* KM71. However, the reported expression of glycosylated BRL in *P. pastoris* KM71 was low, as only about 0.6 mg of purified BRL from 500 ml of culture medium could be obtained by LPS-Sepharose CL-4B column chromatography.

Endotoxin detection and removal have large market in drug companies. Global pharmaceutical diagnosis market continues to grow annually. However, current diagnoses of pathogens heavily rely on conventional bacteria culture and colony counting methods which are labor- and time-consuming. For pathogenic bacteria inhibition, antibiotics are potent antibacterial agents with high specificity. However, the relentless emergence of antibiotic-resistant strains of pathogens, together with the retarded discovery of novel antibacterial agents has led to the need to find alternative treatments. Development of new strategies for pathogenic bacteria detection and treatment is required.

SUMMARY OF THE INVENTION

Figure 1:
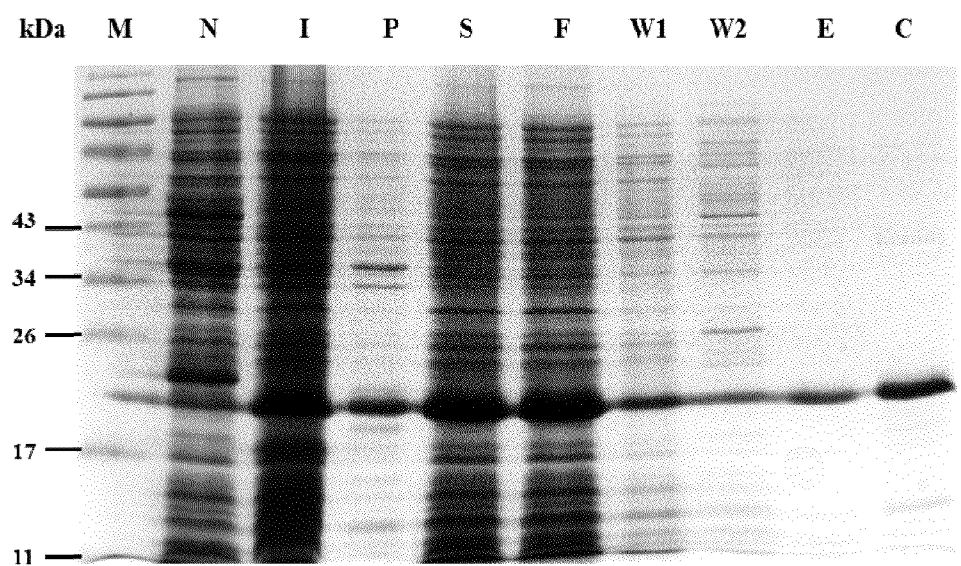
FIG. 1 shows purification and characterization of recombinant bacteria recognizing lectin (rBRL). After induction with 0.1 mM IPTG at 16° C. for 16 h, the supernatant of cell lysate containing rBRL is collected by centrifugation and subjected to Nickel column chromatography for purification. Aliquots of each fraction are analyzed by 15% (w/v) SDS-PAGE. Lane M: molecular weight marker; Lane N: cell lysate of *E. coli* without IPTG induction; Lane I: cell lysate of *E. coli* with IPTG induction; Lane P: insoluble pellet; Lane S: supernatant; Lane F: binding flow-through; Lane W1: washing fraction with 20 mM Tris-HCl, 200 mM NaCl, 5 mM imidazole; Lane W2: washing fraction with 20 mM Tris-HCl, 200 mM NaCl, 50 mM imidazole; Lane E: eluting fraction with 20 mM Tris-HCl, 200 mM NaCl, 300 mM imidazole; Lane C: concentrated fraction.

The present invention relates to a recombinant protein comprising SEQ ID NO: 1 and a bacteria recognizing lectin. The present invention also relates to uses of the recombinant protein comprising detecting pathogens, removing endotoxins, determining the presence of an endotoxin or endotoxin-like material, and determining the presence of pathogen-associated molecular pattern (PAMP) comprising rhamnose-rhamnose (Rha-Rha), rhamnose-N-acetyl-mannosamine (Rha-ManNAc), N-acetyl-mannosamine-rhamnose (ManNAc-Rha), rhamnose-galatose (Rha-Gal), or galatose-rhamnose (Gal-Rha) in a sample, and use as a medicament, a disinfectant, a decontaminant, a surfactant or a diagnostic means. The present invention further relates to a method for prevention and/or treatment of conditions related to pathogen related infections in a patient in need thereof comprising: administering to said patient a pharmaceutically effective amount of composition comprising the recombinant protein, wherein the recombinant protein functions as an antagonist of PAMP comprising Rha-Rha, Rha-ManNAc, ManNAc-Rha, Rha-Gal, or Gal-Rha.

DETAILED DESCRIPTION OF THE INVENTION

Fusion protein approach may overcome the low expression obstacle using affinity tags for increasing protein expression, and aiding in protein purification efficiency.

An artificial peptide was designed to increase solubility of a target fusion protein. An example of the amino acid sequence of such artificial peptide includes but is not limited to SKPTTTTTTTTTAPSTSTTTRPSSSEPATFPTGDSTISS (SEQ ID NO: 1).

Horseshoe crab bacteria recognizing lectin (BRL) derived from hemocytes of *T. tridentatus* is a LPS-binding protein isolated from Taiwanese *T. tridentatus*. An example of the amino acid sequence of BRL includes but is not limited to EDDCTCVTDRSLEGKLMKHPSTPAVY-QILDGCRRLVPNPPTYNNIYKNWECIQ SNILEKLLCK-CDSLSNGAELIKGSGDTVYLL-SNGVKRPIADPETFNGFCFDWN KIKTYSDIVINSLSTGPIIIIK (SEQ ID NO: 2).

In this study, a novel recombinant protein rBRL comprising an N-terminal 39-amino acid artificial peptide and a C-terminal 128-amino acid BRL, (for example: MSKPTTTTTTTTTAPSTSTTTRPSSSE-PATFPTGDSTISSEFEDDCTCVTDRSLEG KLMKHPST-PAVYQILDGCRRLVPNPPTYNNIYKNWE-CIQSNILEKLLCKCDSLS NGAELIKGSGDTVYLLSNGVKRPIAD-PETFNGFCFDWNKIKTYSDIVINSLSTG PIIIIKHHH-HHH (SEQ ID NO: 3)), has been created in *E. coli* expression system. The 1$^{st}$ amino acid residue (M) and the 41$^{th}$ to 42$^{th}$ amino acid residues (EF) of SEQ ID NO: 3 are residues derived from vector pET23a and may be altered when different vector is used, even can be absent in one aspect of the present invention. In addition, the 6 residues (HHHHHH) at the end of SEQ ID NO: 3 functions as a tag for purification and can be replaced by any other sequence having similar function, even can be absent in one aspect of the present invention. According the above, it is noted that the present invention also provides a kind of rBRL which consists of the amino acid sequence of SEQ ID NO: 4 (SKPTTTTTTTT-TAPSTSTTTRPSSSEPATFPTGDS-TISSEDDCTCVTDRSLEGKL MKHPSTPAVY-QILDGCRRLVPNPPTYNNIYKNWECIQSNILEKL LCKCDSLSNG AELIKGSGDTVYLLSNGVKRPIAD-PETFNGFCFDWNKIKTYSDIVINSLSTGPIII IK).

It is noted that any mutation of the above amino acid sequences with the similar activities is involved in the scope of the present invention.

Addition of artificial peptide has successfully enhanced BRL expression and simplified the purification process. rBRL retained LPS- and lipoteichoic acid (LTA)-binding activity and surprisingly, through comparison among those BRL-binding LPS and LTA moieties, it is supposed that pathogen-associated molecular pattern (PAMP) comprising rhamnose-rhamnose (Rha-Rha), rhamnose-N-acetyl-mannosamine (Rha-ManNAc), N-acetyl-mannosamine-rhamnose (ManNAc-Rha), rhamnose-galatose (Rha-Gal), or galatose-rhamnose (Gal-Rha) in a sample plays an important role for BRL reorganization. Regarding antibacterial activity, the growth of *P. aeruginosa* PAO1 is significantly inhibited by rBRL in a dose-dependent manner with an $IC_{50}$ value of 4.3 μM, possibly due to rBRL recognition on specific surface component of bacterium. This engineered rBRL may be developed as a detection agent and also an antibacterial agent for pathogenic bacteria with PAMP comprising Rha-Rha, Rha-ManNAc, ManNAc-Rha, Rha-Gal, or Gal-Rha in a sample on cell surface, such as *Mycobacterium tuberculosis* and *Bacillus anthracis*.

The terms used in the description herein will have their ordinary and common meaning as understood by those skilled in the art, unless specifically defined otherwise.

Thus, the present invention provides an isolated peptide consisting of the amino acid sequence of SEQ ID NO: 1. The present invention also provides a method for increasing expression of a target protein by using SEQ ID NO: 1, comprising (a) fusing SEQ ID NO: 1 with the target protein to form a recombinant protein; and (b) expressing the recombinant protein by an expression host. Preferably, the target protein is bacteria recognizing lectin (BRL) derived from *Tachypleus*, and the expression host is a bacterium, a yeast, an insect cell or a mammalian cell. More preferably, the bacterium is *E. coli*. The method not only simplifies the purification process for the target protein but also retains activity of the target protein after fusing the SEQ ID NO: 1 to the target protein.

The present invention also provides a recombinant protein comprising SEQ ID NO: 1 and a bacteria recognizing lectin (BRL). In a preferred embodiment, the SEQ ID NO: 1 is at N-terminus and the bacteria recognizing lectin is at C-terminus. Preferably, the bacteria recognizing lectin is a horseshoe crab bacteria recognizing lectin derived from *Tachypleus tridentatus*. More preferably, the bacteria recognizing lectin consists of the amino acid sequence of SEQ ID NO: 2. In a preferred embodiment, the recombinant protein consists of the amino acid sequence of SEQ ID NO: 3. In another embodiment, the recombinant protein consists of the amino acid sequence of SEQ ID NO: 4.

The present invention further provides a method for detecting a pathogen in a sample, comprising contacting the sample with the above recombinant protein labeled by a labeling substance to give a complex of the labeled recombinant protein and pathogen, and measuring the labeling substance in the complex to detect the pathogen. Preferably, the pathogen comprises lipoteichoic acid (LTA), lipopolysaccharide (LPS), or pathogen-associated molecular pattern (PAMP) or any combination thereof on the surface. More preferably, the pathogen-associated molecular pattern comprises rhamnose-rhamnose (Rha-Rha), rhamnose-N-acetyl-mannosamine (Rha-ManNAc), N-acetyl-mannosamine-rhamnose (ManNAc-Rha), rhamnose-galatose (Rha-Gal), or galatose-rhamnose (Gal-Rha). In a preferred embodiment, the pathogen is a bacterium. Preferably, the bacterium is selected from the group consisting of *Salmonella* species, *Klebsiella oxytoca, Klebsiella pneumoniae, Klebsiella* I-714, *Acinetobacter baumannii, Pseudomonas aeruginosa, Streptococcus pneumoniae, Listeria monocytogenes, E. coli, Salmonella enterica serovar typhimurium, Serratia marcesens, Staphylococcus aureus, Streptococcus faecalis, Enterococcus faecalis, Shigella* species, *Vibrio cholerae, Streptococcus mutans, Bacillus cereus* and its spore, *Bacillus thuringiensis* and its spore, *Bacillus anthracis* and its spore, *Brevibacterium permense* VKM Ac-2280, *Mycobacterium tuberculosis*, and *Bacillus anthracis*. More preferably, the bacterium is selected from the group consisting of *Salmonella* serogroup C, *Klebsiella oxytoca, Acinetobacter baumannii, Pseudomonas aeruginosa, Streptococcus pneumoniae* serotype 19F, *Streptococcus*

*pneumoniae* serotype 19A, *Streptococcus pneumoniae* serotype 19B, *Streptococcus pneumoniae* serotype 23F, *Pseudomonas aeruginosa* strain PAO1, *Listeria monocytogenes, E. coli, Salmonella enterica* serovar *typhimurium, Serratia marcesens, Staphylococcus aureus, Streptococcus faecalis* and *Enterococcus faecalis*.

The present invention yet provides a method for removing endotoxins from a sample, comprising the steps: (a) incubating or contacting the above recombinant protein to a sample unspecifically or directly immobilized to a solid carrier, wherein the above recombinant proteins is able to bind endotoxin to give a complex of the recombinant protein and endotoxin, and (b) separating the complex from the sample.

The present invention yet provides a method of determining the presence of an endotoxin or endotoxin-like material in a sample, comprising contacting the sample with the above recombinant protein labeled by a labeling substance to give a complex of the labeled recombinant protein and endotoxin, and measuring the labeling substance in the complex to detect the endotoxin. Preferably, the endotoxin or endotoxin-like material is selected from endotoxins or surface antigens from microorganisms such as gram-negative or gram-positive bacteria, fungi, yeasts and algae.

The present invention yet provides a method of determining the presence of a pathogen-associated molecular pattern (PAMP) comprising Rha-Rha, Rha-ManNAc, ManNAc-Rha, Rha-Gal, or Gal-Rha in a sample, comprising contacting the sample with the above recombinant protein labeled by a labeling substance to give a complex of the labeled recombinant protein and PAMP, and measuring the labeling substance in the complex to detect the PAMP.

The present invention yet provides a method for prevention and/or treatment of conditions related to pathogen related infections in a patient in need thereof comprising: administering to said patient a pharmaceutically effective amount of composition comprising the above recombinant protein, wherein the recombinant protein functions as an antagonist of PAMP comprising Rha-Rha, Rha-ManNAc, ManNAc-Rha, Rha-Gal, or Gal-Rha.

The present invention yet provides a use of the recombinant protein of the present invention as a medicament, as a disinfectant in medical, public or private environment, as a decontaminant of bacterial contamination in food industry, animal feed or cosmetic industry, as a surfactant against bacterially contaminated surfaces, or as a diagnostic means in the medicine, food or feed diagnostic or environmental diagnostic.

EXAMPLES

The examples below are non-limiting and are merely representative of various aspects and features of the present invention.

Example 1

Materials and Methods

Reagents

*E. coli* Top10F' (Invitrogen) was used for vector construction and DNA manipulation, *E. coli* expression strain Rosetta (DE3) (Stratagene), vectors pET23a purchased from Novagen were used for protein expression. *Enterobacter aerogenes* ATCC 13048, *Listeria monocytogenes* ATCC 7644, *Shigella flexneri* group B ATCC 12022, *Proteus micrabilis* ATCC 7002, *Serratia marcesens* ATCC 8100, and *Staphylococcus aureus* ATCC 33591 were purchased from Creative Microbiologicals, Ltd, Taiwan. *Pseudomonas aeruginosa* PAO1 and *Klebsiella pneumoniae* CG43 were kindly provided by Dr. Hwan-You Chang (College of Life Science, National Tsing Hua University, Hsinchu, Taiwan). *E. coli O*26:B6, *E. coli* O55:B5, *Pseudomonas aeruginosa* PAO1, *Salmonella enterica* serovar *typhimurium* LPSs, *Staphylococcus aureus* and *Streptococcus faecalis* LTA were purchased from Sigma. All other buffers and reagents are of the highest commercial purity.

Protein Expression and Purification

DNA fragment encoding SEQ ID NO: 1 was amplified by PCR with primers 5' NdeI-ANP (5' CATATGTCCAAGCCACTACTACTAC 3') (SEQ ID NO: 5) and 3' EcoRI-ANP (5' GAATTCTGAGGAGATTGTAGAGTCACC 3') (SEQ ID NO: 6). DNA fragment encoding BRL (SEQ ID NO: 2) was amplified by PCR using cDNA which reverse-transcribed from *Tachypleus tridentatus'* RNA as template. Primers 5' EcoRI-BRL (5' GAATTCGAAGATGACTGCACGTGACAGAC 3') (SEQ ID NO: 7) and 3' NotI-BRL-6His (5' GCGGCCGCTTAATGATGATGATGATGATGC TTAATTATTATAATAGGTCC 3') (SEQ ID NO: 8) were used for amplification of BRL. Two purified PCR products were digested with NdeI/EcoRI and EcoRI/NotI respectively, ligated with pET23a treated with same restriction enzymes. The recombinant plasmid was confirmed by sequencing and then transformed to *E. coli* Top10F' and selected on agar plate containing 100 μg/ml Ampicillin. A single colony picked on the selection plate was grown in 5 ml of Luria-Bertani (LB) medium (1% tryptone, 0.5% yeast extract, and 0.5% sodium chloride) containing the same concentration of the antibiotic at 37° C. overnight for plasmid extraction. The extracted plasmid was then transformed into *E. coli* expression strain Rosetta (DE3) and selected on agar plate containing 100 μg/ml Ampicillin. A single colony was picked and grown in 1 L LB medium at 37° C. until $OD_{600}$ reached 0.4 to 0.6. Protein expression was induced by addition of IPTG to a final concentration of 0.1 mM and incubation at 16° C. for 16 h. Cells were harvested by centrifugation at 4000×g for 10 min at 4° C., and washed once with PBS. Then, the cell pellet was resuspended in 50 mL of equilibrium buffer (20 mM Tris-HCl, 200 mM NaCl, 5 mM imidazole, pH 7.4) supplemented with protease inhibitor (1 mM phenylmethylsulfonyl fluoride, PMSF) and disrupted by a 3-fold passage through a cell homogenizer at 15,000 psi. The cell lysate was separated into supernatant and pellet by centrifugation at 16000×g for 30 min at 4° C. The supernatant was subjected to purification by Ni Sepharose™ 6 Fast Flow (GE healthcare) column chromatography. The column was first pre-equilibrated with equilibrium buffer and at the end of sample loading, washed with 50 mL equilibrium buffer (W1) and 50 mL wash buffer (20 mM Tris-HCl, 200 mM NaCl, 50 mM imidazole, pH 7.4) (W2). To recover bound protein, the column was eluted with elution buffer (20 mM Tris-HCl, 200 mM NaCl, 300 mM imidazole, pH 7.4). The eluted rBRL was then concentrated and buffer-exchanged to Tris buffer (20 mM Tris-HCl, 200 mM NaCl, pH 7.4).

Bacteria- and PAMP-Binding ELISA

A suspension of 50 μl bacteria ($5\times10^7$ cells/well), LPS or LTA at indicated concentration in serial dilution in coating buffer (mixture of chloroform and ethanol (1:9 (v/v)) for bacteria and 0.1 M sodium carbonate-bicarbonate buffer, pH 9.6 for LPS/LTA) was added to 96-well microplates and incubated at 4° C. overnight. The concentration of bacteria in the culture was determined by measuring the scattered light of the culture at an optical density of 600 nm with a spectrophotometer (Hitachi U-3310). Number of cells/ml was estimated by assuming that 0.1 optical density unit was roughly equivalent to $10^8$ cells/ml. Microplates with the immobilized bacteria or PAMPs were washed three times with wash buffer (0.05% Tween 20 in phosphate-buffered saline (PBST)), and the unbound regions were blocked with blocking buffer (3% non-fat milk in PBST) at 37° C. for 2 h. Following this, fifty microliters of 1 μM purified rBRL was added to each well and incubated at 37° C. for 1.5 h. Equilibrium buffer used for protein purification was added in parallel as negative control.

After washing three times with wash buffer, anti-His monoclonal antibody (Clontech) (1:5000) was added to each well and incubated at 37° C. for 1 h. Subsequently, horseradish peroxidase-conjugated monoclonal anti-mouse IgG antibody (Jackson) (1:5000) was added to each well after washing three times with wash buffer and incubated at 37° C. for 30 min. Then 100 μl of 3,3',5,5'-tetramethylbenzidine (TMB) substrate (KPL) was added to each well after washing three times with wash buffer, and incubated at 37° C. for exactly 15 min. Finally, the reaction was terminated by the addition of 100 μl of 2 N $H_2SO_4$. The absorbance at 450 nm was read with spectrophotometer (Thermo max microplate reader).

Antibacterial Activity Assay

*Pseudomonas aeruginosa* PAO1, *Listeria monocytogenes* and *Staphylococcus aureus* were incubated in LB medium at 37° C. overnight. The cells were subcultured (1:100) and grow at 37° C. for 4 h. The LB medium was substituted with 10 mM sodium phosphate buffer (pH 7.4) and then washed for three times with the buffer. After washing, the cell count was determined by the spectrophotometric method at a wavelength of 600 nm. A 25 μL $10^6$ cells/ml bacteria was mixed with 25 μL of 0 μM, 0.4875 μM, 0.9374 μM, 1.875 μM, 3.75 μM, 7.5 μM, and 15 μM rBRL dissolved in sodium phosphate buffer (pH 7.4) and incubated at 37° C. for 4 h. Afterwards, one quarter of the volume was applied on LB agar plates and incubated at 37° C. for approximately 16 h. By observing the decreasing colony number, cell mortality could be calculated compared to control plate.

Results

Expression and Purification of rBRL rBRL was composed of an artificial N-terminal peptide and a C-terminal horseshoe crab bacteria recognizing lectin (BRL) derived from *T. tridentatus*. DNA fragments encoding artificial peptide and BRL were separately ligated into pET23a vector and the recombinant plasmid was transformed into *E. coli* Rosetta (DE3) for protein expression. From 1 L of culture medium, approximately 6 mg of purified rBRL was obtained by Nickel column chromatography, with a recovery rate of 80.6% (FIG. 1). Five-fold higher yield of rBRL than BRL-6His has been achieved; indicating that the artificial peptide fused at the N-terminal end of BRL has successfully facilitated the isolation of rBRL.

Binding of rBRL to LPS

Figure 2:
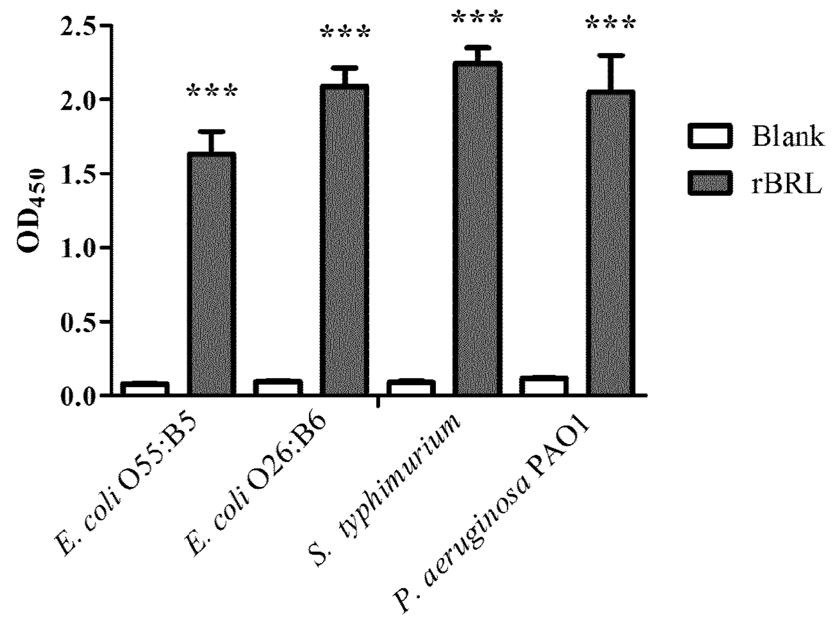
FIGS. 2A and 2B show PAMP binding activity of rBRL. A total of 0.5 μg of each (A) LPS or (B) LTA is coated on the microplate wells and detected with 1 μM rBRL. Anti-His monoclonal antibody (1:5000) is used to detect rBRL binding to LPS or LTA. Blank refers to the wells added with buffer instead of rBRL. All data represent means of triplicate incubations. The error bars show standard deviations in triplicate experiments (***$p<0.001$).
Figure 2:
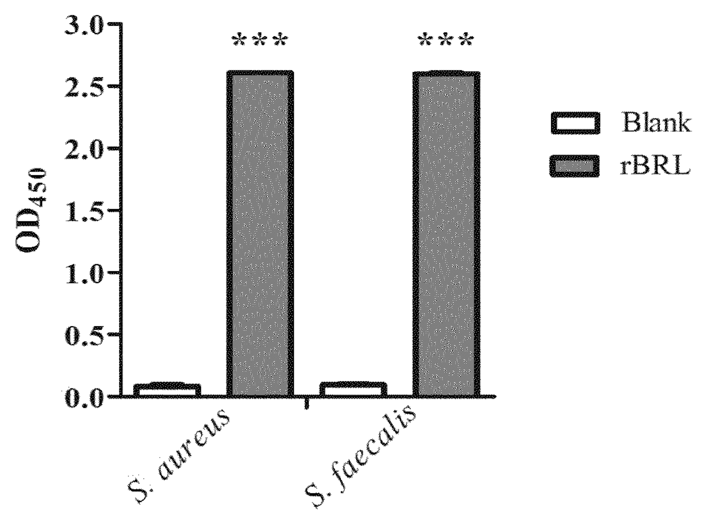

Previously, BRL-6His expressed by *P. pastoris* KM71 was purified by *E. coli* O26:B6 LPS-Sepharose CL-4B, indicating that BRL was able to bind to *E. coli* O26:B6 LPS. To verify LPS and LTA binding activity of rBRL, four different LPSs from *E. coli* O26:B6, *E. coli* O55:B5, *Pseudomonas aeruginosa* PAO1 and *Salmonella enterica* serovar *typhimurium*, and also two LTAs form *Staphylococcus aureus* and *Streptococcus faecalis* were tested by ELISA. As shown in FIGS. 2A and 2B, rBRL bound to all four LPSs and two LTAs significantly, indicating that addition of an artificial peptide fusion head at the N-terminus of BRL does not influence the LPS-binding capacity of BRL.

Binding of rBRL to Gram-Negative and Gram-Positive Bacteria

Figure 3:
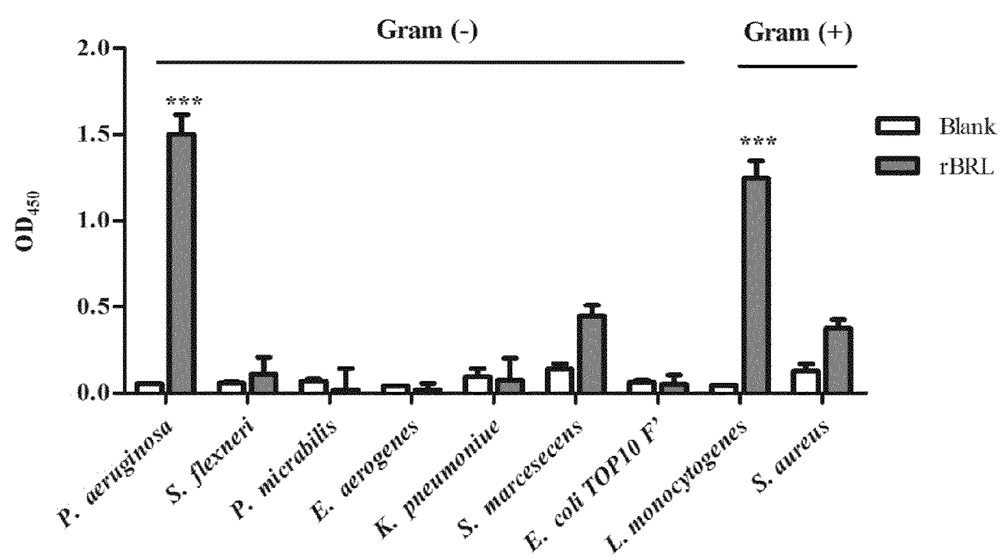
FIG. 3 shows Gram-negative and Gram-positive bacteria binding activities of rBRL. Bacterial cells are seeded at $5\times10^7$ cells per well and then 1 μM of rBRL is applied to the wells of the bacteria cells-immobilized microplate. Subsequently, anti-His monoclonal antibody (1:5000) is used to detect rBRL bound to bacteria cells. Blank refers to the wells added with buffer instead of rBRL. All data represent means of triplicate incubations. The error bars show standard deviations in triplicate experiments (***$p<0.001$).

To further confirm rBRL binding to Gram-negative bacteria, here seven different Gram-negative bacteria including *Pseudomonas aeruginosa, Shigella flexneri, Proteus micrabilis, Enterobacter aerogenes, Klebsiella pneumoniae, Serratia marcescens*, and *E. coli* TOP 10F', as well as two Gram-positive bacteria including *Staphylococcus aureus* and *Listeria monocytogenes*, were tested employing bacterial binding ELISA. FIG. 3 revealed that rBRL significantly and selectively bound to Gram-negative *Pseudomonas aeruginosa* and Gram-positive *Listeria monocytogenes. Serratia marcesens* and *Staphylococcus aureus* also showed weak binding, but the other bacteria did not.

Pathogen Recognition of rBRL

Figure 4:
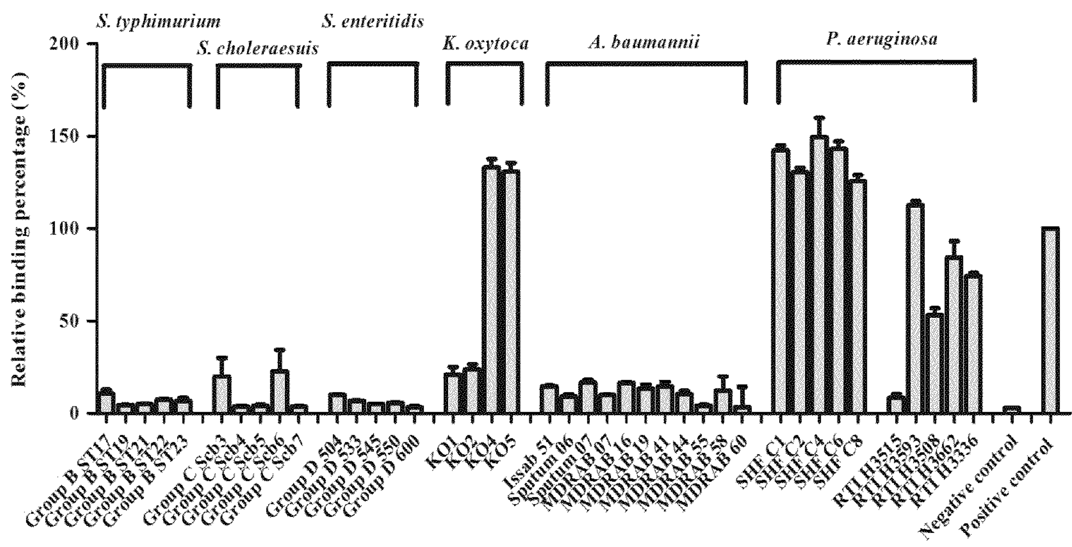
FIGS. 4A and 4B show pathogen recognition of rBRL. (A) Gram-negative bacteria and (B) Gram-positive bacteria are seeded at $5\times10^7$ cells per well and then 1 μM of rBRL is applied to the wells of the bacteria cells-immobilized microplate. Subsequently, anti-His monoclonal antibody (1:5000) is used to detect rBRL bound to bacteria cells. Blank refers to the wells added with buffer instead of rBRL. The amount of 1 μM rBRL bound to *Pseudomonas aeruginosa* PAO1 LPS is used as positive control and set as 100% binding ability. All data represent means of triplicate incubations.
Figure 4:
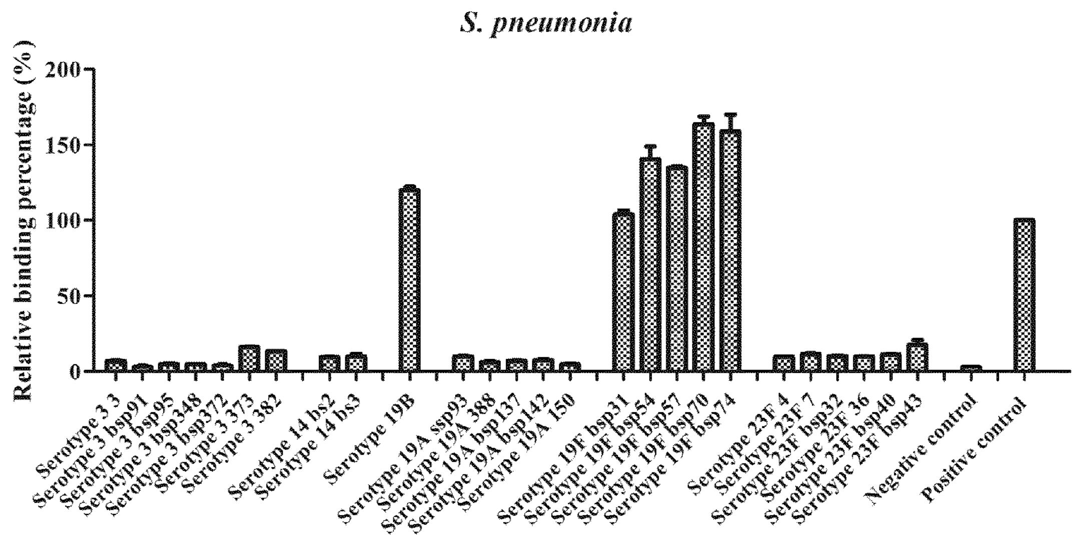

Understanding of specific rBRL interaction with bacteria as well as pathogens would lead to development of novel diagnostic strategies to detect microbial pathogens such as infectious bacteria from clinical site, for example, *Staphylococcus aureus, Pseudomonas aeruginosa, Klebsiella pneumoniae, Salmonella enterica* etc. Here several clinically isolated microbial pathogens were used to examine the pathogen-binding activity of rBRL. As shown in FIG. 4A, Gram-negative bacteria *Klebsiella oxytoca, Acinetobacter baumannii*, and *Pseudomonas aeruginosa* were recognized by rBRL, especially *Klebsiella oxytoca KO*4, KO5, and *Acinetobacter baumannii* AB199, and *Pseudomonas aeruginosa* C1, C2, C4, C6 and C8. For Gram-positive bacteria, rBRL specifically recognized *Streptococcus pneumoniae* serogroup 19B and 19F (FIG. 4B).

Growth-Inhibitory Effect of rBRL on Pathogens

Figure 5:
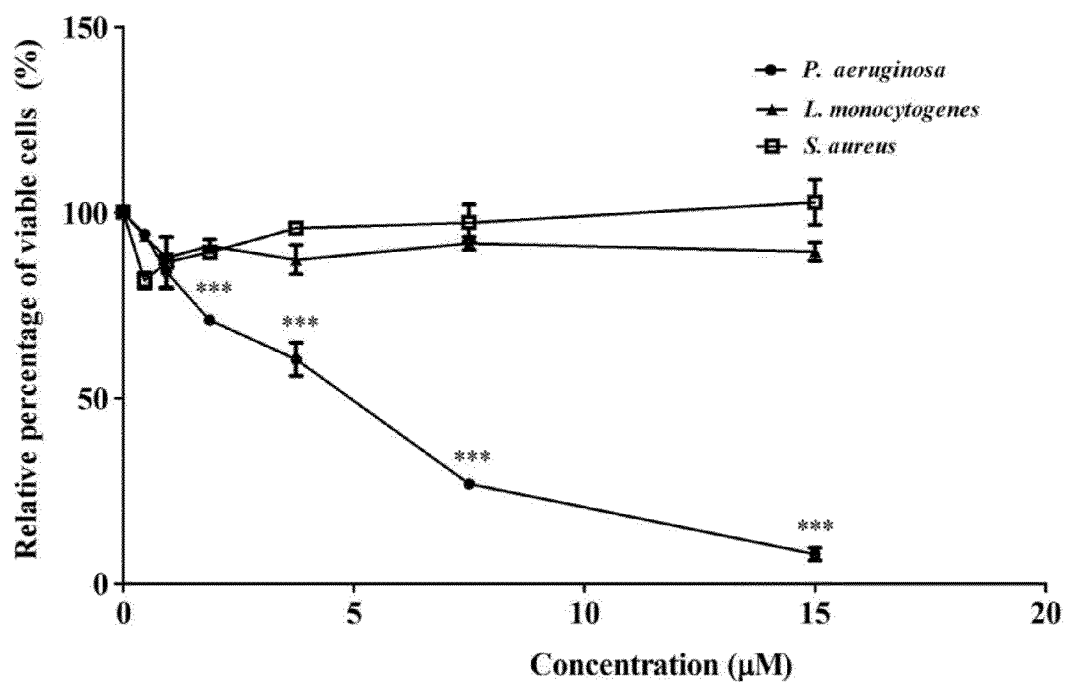
FIG. 5 shows inhibitory effect of rBRL on the growth of *Pseudomonas aeruginosa*. Bacterial cells are incubated in LB at 37° C. overnight. The cells are subcultured in 1:100 dilution folds and allowed to grow at 37° C. for 4 h. A 25 μL $1\times10^6$ cells/ml bacteria is mixed with 25 μL of 0 μM, 1.875 μM, 3.75 μM, 7.5 μM, and 15 μM rBRL dissolved in sodium phosphate buffer (pH 7.4) and incubated at 37° C. for 4 h. The growth-inhibitory activity of rBRL is analyzed by plating a quarter of incubation mixture and the CFU is counted on the following day. Cell mortality is calculated as decrease of the colony number compared to the control plate. The data represents the means of triplicate experiment and the error bars show standard deviations among triplicate experiments (***$p<0.001$).

To investigate antibacterial activity of rBRL, *P. aeruginosa* PAO1, *L. monocytogenes* ATCC 7644 and *S. aureus* ATCC 33591 were examined. A 25 μL of $1\times10^6$ cells/ml bacteria was mixed with 25 μL of 0 μM (buffer only), 0.46875 μM, 0.9365, μM 1.875 μM, 3.75 μM, 7.5 μM, or 15 μM rBRL that dissolved in sodium phosphate buffer (pH 7.4) and incubated at 37° C. for 4 h. Growth-inhibitory activity of rBRL was analyzed by plating serial dilutions of the incubation mixture and colony. FIG. 5 showed rBRL inhibited *P. aeruginosa* growth in a dose-dependent manner, and the $LC_{50}$ value was at concentration of 4.305 μM.

LPS, the major component of the outer membrane of Gram-negative bacteria, is an amphiphatic large molecule consisting of a hydrophobic lipid and a hydrophilic polysaccharide joined by a covalent bond. Previously, the O-antigen of certain LPS has been demonstrated to serve as the specific ligand for rBRL. Interestingly, comparison among chemical structures of PAMP of rBRL binding bacteria (Table 1) showed that composition of Rha-Rha, Rha-ManNAc, ManNAc-Rha, Rha-Gal, or Gal-Rha was a common component in PAMP moieties, hence they were deemed ligands for rBRL binding to these LPSs.

TABLE 1

| Bacteria strains | LPS structures |
|---|---|
| *Acinetobacter baumannii* serogroup O10 | α-D-Man*p*Nac<br>1<br>↓<br>3<br>→-3)-α-D-Glc*p*Nac-(1→2)-α-L=Rha*p*-(1→2)-α-L-Rha*p*-(1→3)-α-L-Rha*p*-(1→ |
| *Klebsiella oxytoca* strain TMN3 | -2)-α-L-Rha-(1→2)-α-D-Glc-(1→3)-β-Gal-(1→3)-α-D-GlcUA-(1→2)-α-L-Rha-(1→<br>4<br>↓<br>1<br>α-L-Rha |

TABLE 1-continued

| Bacteria strains | LPS structures |
|---|---|
| *Pseudomonas aeruginosa* | A band:<br>→3)-α-D-Rha-(1→2)-α-D-Rha-(1→3)-α-D-Rha-(1→ |
| *Salmonella enterica* serogroup C2 | 2OAc-α-D-Abe 2-OAc-α-D-Glc<br>1 1<br>↓ ↓<br>3 4<br>→4)-β-L-Rha-(1→2)-α-Man-(1→2)-α-D-Man-(1→3)-β-D-Gal-(1 → |
| *Streptococcus pneumoniae* serogroup 19B | →4)-β-D-ManNAc-(1→4)-α-L-Rhap-(1→4)-β-D-ManNAc-(1→4)-β-D-Glc-(1→<br>3<br>↑<br>1<br>B-D-Rib-(1→4)-α-L-Rha |
| *Streptococcus pneumoniae* serogroup 19F | →2)-α-L-Rhap-(1→4)-β-D-ManNAc-(1→4)-α-D-Glc-(1→ |

One skilled in the art readily appreciates that the present invention is well adapted to carry out the objects and obtain the ends and advantages mentioned, as well as those inherent therein. The peptide, recombinant protein, processes and methods for producing them and their uses are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A recombinant protein comprising:

an artificial peptide consisting of the amino acid sequence of SEQ ID NO: 1; and a bacteria recognizing lectin.

2. The recombinant protein of claim 1, wherein the SEQ ID NO: 1 is at N-terminus and the bacteria recognizing lectin is at C-terminus.

3. The recombinant protein of claim 1, wherein the bacteria recognizing lectin consists of the amino acid sequence of SEQ ID NO: 2.

4. The recombinant protein of claim 1, which consists of the amino acid sequence of SEQ ID NO: 3.

5. The recombinant protein of claim 1, which consists of the amino acid sequence of SEQ ID NO: 4.

6. The recombinant protein of claim 1, which is used for detecting a pathogen in a sample by the steps comprising: contacting the sample with the recombinant protein labeled by a labeling substance to give a complex of the labeled recombinant protein and pathogen, and measuring the labeling substance in the complex to detect the pathogen.

7. The recombinant protein of claim 6, wherein the pathogen comprises lipoteichoic acid, lipopolysaccharide or pathogen-associated molecular pattern or any combination thereof on the surface.

8. The recombinant protein of claim 7, wherein the pathogen-associated molecular pattern comprises rhamnose-rhamnose, rhamnose-N-acetyl-mannosamine, N-acetyl-mannosamine-rhamnose, rhamnose-galatose, or galatose-rhamnose.

9. The recombinant protein of claim 6, wherein the pathogen is a bacterium.

10. The recombinant protein of claim 9, wherein the bacterium is selected from the group consisting of *Salmonella* species, *Klebsiella oxytoca, Klebsiella pneumoniae, Klebsiella* I-714, *Acinetobacter baumannii, Pseudomonas aeruginosa, Streptococcus pneumoniae, Listeria monocytogenes, E. coli, Salmonella enterica serovar typhimurium, Serratia marcesens, Staphylococcus aureus, Streptococcus faecalis, Enterococcus faecalis, Shigella* species, *Vibrio cholerae, Streptococcus mutans, Bacillus cereus* and its spore, *Bacillus thuringiensis* and its spore, *Bacillus anthracis* and its spore, *Brevibacterium permense* VKM Ac-2280, and *Mycobacterium tuberculosis.*

11. The recombinant protein of claim 9, wherein the bacterium is selected from the group consisting of *Salmonella* serogroup C, *Klebsiella oxytoca, Acinetobacter baumannii, Pseudomonas aeruginosa, Streptococcus pneumoniae* serotype19F, *Streptococcus pneumoniae* serotype 19A, *Streptococcus pneumoniae* serotype 19B, *Streptococcus pneumoniae* serotype 23F, *Pseudomonas aeruginosa* strain PAO1, *Listeria monocytogenes, E. coli, Salmonella enterica serovar typhimurium, Serratia marcesens, Staphylococcus aureus, Streptococcus faecalis*, and *Enterococcus faecalis.*

12. The recombinant protein of claim 1, which is used for removing endotoxins from a sample by the steps comprising: a) incubating or contacting the recombinant protein to a sample unspecifically or directly immobilized to a solid carrier, wherein the recombinant protein is able to bind endotoxin to give a complex of the recombinant protein and endotoxin, and b) separating the complex from the sample.

13. The recombinant protein of claim 1, which is used for determining the presence of an endotoxin or endotoxin-like material in a sample by the steps comprising: contacting the sample with the recombinant protein labeled by a labeling substance to give a complex of the labeled recombinant protein and endotoxin, and measuring the labeling substance in the complex to detect the endotoxin.

14. The recombinant protein of claim 13, wherein the endotoxin or endotoxin-like material is selected from endotoxins or surface antigens from microorganisms such as gram-negative or gram-positive bacteria, fungi, yeasts and algae.

15. The recombinant protein of claim 1, which is used for determining the presence of rhamnose by the steps comprising: contacting the sample with the recombinant protein labeled by a labeling substance to give a complex of the labeled recombinant protein and rhamnose, and measuring the labeling substance in the complex to detect the rhamnose.

16. The recombinant protein of claim 15, wherein the rhamnose is involved in a pathogen-associated molecular pattern.

17. The recombinant protein of claim 16, wherein the pathogen-associated molecular pattern comprises rhamnose-rhamnose, rhamnose-N-acetyl-mannosamine, N-acetyl-mannosamine-rhamnose, rhamnose-galatose, or galatose-rhamnose.

18. The recombinant protein of claim 1, which is used for prevention and/or treatment of conditions related to pathogen related infections in a patient in need thereof by the steps comprising: administering to said patient a pharmaceutically effective amount of a composition comprising the recombinant protein, wherein the recombinant protein functions as an antagonist of pathogen-associated molecular pattern comprising rhamnose-rhamnose, rhamnose-N-acetyl-mannosamine, N-acetyl-mannosamine-rhamnose, rhamnose-galatose, or galatose-rhamnose.

19. The recombinant protein of claim 1, which is used for inhibiting growth of a pathogen in a subject or in an environment by the steps comprising: applying a composition comprising the recombinant protein to the subject or the environment, in an amount effective to inhibit the growth of the pathogen.

20. The recombinant protein of claim 19, wherein the pathogen is *Pseudomonas aeruginosa*.

21. The recombinant protein of claim 1, which is used as a medicament.

22. The recombinant protein of claim 1, which is used as a disinfectant in medical, public or private environment, as a decontaminant of bacterial contamination in food industry, animal feed or cosmetic industry or as a surfactant against bacterially contaminated surfaces.

23. The recombinant protein of claim 1, which is used as a diagnostic means in the medicine, food or feed diagnostic or environmental diagnostic.

* * * * *

SEQUENCE LISTING

<160> NUMBER OF SEQ ID NOS: 8

<210> SEQ ID NO 1
<211> LENGTH: 39
<212> TYPE: PRT
<213> ORGANISM: Artificial Sequence
<220> FEATURE:
<223> OTHER INFORMATION: Solubility enhancing peptide.
<220> FEATURE:
<221> NAME/KEY: PEPTIDE
<222> LOCATION: (1)..(39)

<400> SEQUENCE: 1

Ser Lys Pro Thr Thr Thr Thr Thr Thr Thr Thr Thr Ala Pro Ser Thr
1 5 10 15

Ser Thr Thr Thr Arg Pro Ser Ser Ser Glu Pro Ala Thr Phe Pro Thr
20 25 30

Gly Asp Ser Thr Ile Ser Ser
35

<210> SEQ ID NO 2
<211> LENGTH: 128
<212> TYPE: PRT

<213> ORGANISM: Tachypleus tridentatus
<220> FEATURE:
<221> NAME/KEY: mat_peptide
<222> LOCATION: (1)..(128)

<400> SEQUENCE: 2

Glu Asp Asp Cys Thr Cys Val Thr Asp Arg Ser Leu Glu Gly Lys Leu
1 5 10 15

Met Lys His Pro Ser Thr Pro Ala Val Tyr Gln Ile Leu Asp Gly Cys
20 25 30

Arg Arg Leu Val Pro Asn Pro Pro Thr Tyr Asn Asn Ile Tyr Lys Asn
35 40 45

Trp Glu Cys Ile Gln Ser Asn Ile Leu Glu Lys Leu Leu Cys Lys Cys
50 55 60

Asp Ser Leu Ser Asn Gly Ala Glu Leu Ile Lys Gly Ser Gly Asp Thr
65 70 75 80

Val Tyr Leu Leu Ser Asn Gly Val Lys Arg Pro Ile Ala Asp Pro Glu
85 90 95

Thr Phe Asn Gly Phe Cys Phe Asp Trp Asn Lys Ile Lys Thr Tyr Ser
100 105 110

Asp Ile Val Ile Asn Ser Leu Ser Thr Gly Pro Ile Ile Ile Ile Lys
115 120 125

<210> SEQ ID NO 3
<211> LENGTH: 176
<212> TYPE: PRT
<213> ORGANISM: Artificial Sequence
<220> FEATURE:
<223> OTHER INFORMATION: A novel recombinant protein rBRL comprising an N-terminal 39-amino acid artificial peptide and a C-terminal 128-amino acid BRL.
<220> FEATURE:
<221> NAME/KEY: MISC_FEATURE
<222> LOCATION: (1)..(176)

<400> SEQUENCE: 3

Met Ser Lys Pro Thr Thr Thr Thr Thr Thr Thr Thr Thr Ala Pro Ser
1 5 10 15

Thr Ser Thr Thr Thr Arg Pro Ser Ser Ser Glu Pro Ala Thr Phe Pro
20 25 30

Thr Gly Asp Ser Thr Ile Ser Ser Glu Phe Glu Asp Asp Cys Thr Cys
35 40 45

Val Thr Asp Arg Ser Leu Glu Gly Lys Leu Met Lys His Pro Ser Thr
50 55 60

Pro Ala Val Tyr Gln Ile Leu Asp Gly Cys Arg Arg Leu Val Pro Asn
65 70 75 80

Pro Pro Thr Tyr Asn Asn Ile Tyr Lys Asn Trp Glu Cys Ile Gln Ser
85 90 95

Asn Ile Leu Glu Lys Leu Leu Cys Lys Cys Asp Ser Leu Ser Asn Gly
100 105 110

Ala Glu Leu Ile Lys Gly Ser Gly Asp Thr Val Tyr Leu Leu Ser Asn
115 120 125

Gly Val Lys Arg Pro Ile Ala Asp Pro Glu Thr Phe Asn Gly Phe Cys
130 135 140

Phe Asp Trp Asn Lys Ile Lys Thr Tyr Ser Asp Ile Val Ile Asn Ser
145 150 155 160

Leu Ser Thr Gly Pro Ile Ile Ile Ile Lys His His His His His His
165 170 175

<210> SEQ ID NO 4
<211> LENGTH: 167
<212> TYPE: PRT
<213> ORGANISM: Artificial Sequence
<220> FEATURE:
<223> OTHER INFORMATION: An alternative kind of rBRL.
<220> FEATURE:
<221> NAME/KEY: MISC_FEATURE
<222> LOCATION: (1)..(167)

<400> SEQUENCE: 4

```
Ser Lys Pro Thr Thr Thr Thr Thr Thr Thr Thr Thr Ala Pro Ser Thr
1               5                   10                  15

Ser Thr Thr Thr Arg Pro Ser Ser Ser Glu Pro Ala Thr Phe Pro Thr
            20                  25                  30

Gly Asp Ser Thr Ile Ser Ser Glu Asp Asp Cys Thr Cys Val Thr Asp
        35                  40                  45

Arg Ser Leu Glu Gly Lys Leu Met Lys His Pro Ser Thr Pro Ala Val
    50                  55                  60

Tyr Gln Ile Leu Asp Gly Cys Arg Arg Leu Val Pro Asn Pro Pro Thr
65                  70                  75                  80

Tyr Asn Asn Ile Tyr Lys Asn Trp Glu Cys Ile Gln Ser Asn Ile Leu
                85                  90                  95

Glu Lys Leu Leu Cys Lys Cys Asp Ser Leu Ser Asn Gly Ala Glu Leu
            100                 105                 110

Ile Lys Gly Ser Gly Asp Thr Val Tyr Leu Leu Ser Asn Gly Val Lys
        115                 120                 125

Arg Pro Ile Ala Asp Pro Glu Thr Phe Asn Gly Phe Cys Phe Asp Trp
    130                 135                 140

Asn Lys Ile Lys Thr Tyr Ser Asp Ile Val Ile Asn Ser Leu Ser Thr
145                 150                 155                 160

Gly Pro Ile Ile Ile Ile Lys
                165
```

<210> SEQ ID NO 5
<211> LENGTH: 25
<212> TYPE: DNA
<213> ORGANISM: Artificial Sequence
<220> FEATURE:
<223> OTHER INFORMATION: Primer 5' NdeI-ANP.
<220> FEATURE:
<221> NAME/KEY: primer_bind
<222> LOCATION: (1)..(25)

<400> SEQUENCE: 5

```
catatgtcca agccactact actac                                            25
```

<210> SEQ ID NO 6
<211> LENGTH: 27
<212> TYPE: DNA
<213> ORGANISM: Artificial Sequence
<220> FEATURE:
<223> OTHER INFORMATION: Primer 3' EcoRI-ANP.
<220> FEATURE:
<221> NAME/KEY: primer_bind
<222> LOCATION: (1)..(27)

<400> SEQUENCE: 6

```
gaattctgag gagattgtag agtcacc                                          27
```

<210> SEQ ID NO 7
<211> LENGTH: 29

-continued

```
<212> TYPE: DNA
<213> ORGANISM: Artificial Sequence
<220> FEATURE:
<223> OTHER INFORMATION: Primer 5' EcoRI-BRL.
<220> FEATURE:
<221> NAME/KEY: primer_bind
<222> LOCATION: (1)..(29)

<400> SEQUENCE: 7

gaattcgaag atgactgcac gtgacagac                                   29


<210> SEQ ID NO 8
<211> LENGTH: 50
<212> TYPE: DNA
<213> ORGANISM: Artificial Sequence
<220> FEATURE:
<223> OTHER INFORMATION: Primer 3' NotI-BRL-6His.
<220> FEATURE:
<221> NAME/KEY: primer_bind
<222> LOCATION: (1)..(50)

<400> SEQUENCE: 8

gcggccgctt aatgatgatg atgatgatgc ttaattatta taataggtcc            50
```